United States Patent
Iwase et al.

(10) Patent No.: US 10,413,681 B2
(45) Date of Patent: Sep. 17, 2019

(54) SYRINGE FOR INJECTING DRUG SOLUTION INTO UPPER LAYER OF SKIN

(71) Applicant: TERUMO KABUSHIKI KAISHA, Tokyo (JP)

(72) Inventors: Yoichiro Iwase, Kanagawa (JP); Kazunori Koiwai, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/211,741

(22) Filed: Jul. 15, 2016

(65) Prior Publication Data

US 2016/0317761 A1     Nov. 3, 2016

Related U.S. Application Data

(63) Continuation of application No. PCT/JP2014/080950, filed on Nov. 21, 2014.

(30) Foreign Application Priority Data

Jan. 16, 2014  (JP) ................................. 2014-005888

(51) Int. Cl.
*A61M 5/46*      (2006.01)
*A61B 17/20*     (2006.01)
(Continued)

(52) U.S. Cl.
CPC ............... *A61M 5/46* (2013.01); *A61B 17/20* (2013.01); *A61B 17/205* (2013.01); *A61M 5/28* (2013.01);
(Continued)

(58) Field of Classification Search
CPC ................. A61B 17/20; A61B 17/205; A61M 2005/3107; A61M 2005/3131;
(Continued)

(56) References Cited

U.S. PATENT DOCUMENTS

2007/0118077 A1* 5/2007 Clarke .................. A61M 5/158
                                                                    604/117
2011/0275994 A1* 11/2011 Iwase .................... A61M 5/425
                                                                    604/117
(Continued)

FOREIGN PATENT DOCUMENTS

EP     2 554 199       2/2013
JP     2005-537893 A   12/2005
(Continued)

OTHER PUBLICATIONS

International Search Report for International Patent Application No. PCT/JP2014/080950 dated Mar. 3, 2015.
(Continued)

*Primary Examiner* — Imani N Hayman
(74) *Attorney, Agent, or Firm* — Foley & Lardner LLP (57) ABSTRACT

A syringe for injecting a drug solution into an upper layer of skin includes an injection needle having a needle hole communicating from a needle tip to a needle proximal end, the injection needle having a blade face at the needle tip; and a needle hub having a distal end portion and a proximal end portion, the needle hub holding the injection needle at the distal end portion. The needle hub has a needle tip side end face, and the needle tip protrudes from the needle tip side end face. A protruding needle length of the needle tip from the needle tip side end face is 1.15 mm±0.1 mm, and a blade face length of the blade face along an axis of the injection needle is 0.60 mm±0.15 mm.

8 Claims, 3 Drawing Sheets

(51) Int. Cl.
  *A61M 5/28* (2006.01)
  *A61M 5/31* (2006.01)
  *A61M 5/315* (2006.01)
  *A61M 5/32* (2006.01)
  *A61M 5/00* (2006.01)
  *A61M 5/34* (2006.01)

(52) U.S. Cl.
  CPC ...... *A61M 5/3129* (2013.01); *A61M 5/31511* (2013.01); *A61M 5/3286* (2013.01); *A61M 5/002* (2013.01); *A61M 5/3134* (2013.01); *A61M 5/3293* (2013.01); *A61M 5/347* (2013.01); *A61M 2005/3107* (2013.01); *A61M 2005/3131* (2013.01)

(58) Field of Classification Search
  CPC .. A61M 5/28; A61M 5/3129; A61M 5/31511; A61M 5/32; A61M 5/3286; A61M 5/3293; A61M 5/46
  See application file for complete search history.

(56) References Cited

U.S. PATENT DOCUMENTS

| | | |
|---|---|---|
| 2013/0079729 A1 | 3/2013 | Yokota et al. |
| 2014/0245882 A1 | 9/2014 | Matusch |

FOREIGN PATENT DOCUMENTS

| | | |
|---|---|---|
| JP | 2009-516572 A | 4/2009 |
| JP | 2011-212185 A | 10/2011 |
| JP | 2012-508058 A | 4/2012 |
| WO | WO-2004/024219 A1 | 3/2004 |
| WO | WO-2007/061972 A2 | 5/2007 |
| WO | WO-2010/053570 A1 | 5/2010 |
| WO | WO-2012/153563 A1 | 11/2012 |
| WO | WO-2013/072455 A1 | 5/2013 |

OTHER PUBLICATIONS

Notification of Reasons for Refusal issued in corresponding JP Patent Application No. 2015-557724 dated Aug. 16, 2017.
English Machine Translation of Notification of Reasons for Refusal for Japanese Application No. 2015557724, dated Mar. 16, 2018, 3 pages.
Extended European Search Report issued in corresponding EP application No. 14879228.6 dated Aug. 28, 2017.
Japanese Office Action dated Aug. 30, 2018 in corresponding application No. 2015-557724.

* cited by examiner

SYRINGE FOR INJECTING DRUG SOLUTION INTO UPPER LAYER OF SKIN

CROSS-REFERENCE TO RELATED APPLICATIONS

The present application is a continuation of PCT Application No. PCT/JP2014/080950, filed on Nov. 21, 2014, which claims priority to Japanese Patent Application No. 2014-005888, filed on Jan. 16, 2014. Both of these application are incorporated by reference in their entireties.

BACKGROUND

Technical Field

The present disclosure relates to a syringe that is used to inject a small amount of drug solution such as a vaccine into an upper layer of skin, and particularly into a target site near an epidermic layer in a dermic layer.

Background Art

A drug solution including a biological preparation such as an influenza vaccine is generally subcutaneously administered to subcutaneous tissue of skin, or intramuscularly administered to muscle tissue deeper than the subcutaneous tissue. Recently, it has been revealed that the dose of the vaccine can be reduced by administering the vaccine to an upper layer of skin, that is, a target site, ranging from epidermis to dermis where many immunocompetent cells are present.

Skin includes an epidermic layer having a thickness of 50 to 200 μm from a skin surface, a dermic layer having a thickness of 0.5 to 3.5 mm continuing from the epidermic layer, and a subcutaneous tissue layer deeper than the dermic layer. The immunocompetent cells such as Langerhans cells that exist in an epidermis stratum spinosum layer within the epidermic layer and many intradermal dendritic cells that exist near the epidermic layer in the dermic layer are provided with dendritic projections, have receptors that are responsible for skin immunity, and react to antigens from the outside.

The epidermic layer is very thin because it has the thickness of only 50 to 200 μm from the skin surface. Individual variability in the epidermic layer is large because an epidermic condition and a thickness are different depending on an age difference between adults, youths, infants, and babies, a gender difference, individual differences. Therefore, it is very difficult to selectively inject a very small amount of vaccine equal to or less than 200 μL into the epidermis stratum spinosum layer where the Langerhans cells exist by means of an injection needle much thicker than the thickness of the epidermic layer, which is the only usable injection needle in terms of strength and convenience of manufacture.

Instead of the epidermic layer, if the vaccine can be injected, so that an injection site can be selected from the upper layer of skin ranging from the epidermic layer to the dermic layer, into the epidermis stratum spinosum layer where the Langerhans cells exist or a region near the epidermis in the dermic layer where the intradermal dendritic cells exist, it should be possible to further increase immunity elicitation capability while reducing the dose of the vaccine.

Because the upper layer of skin includes a lot of elastic fibrous tissue such as elastin and collagen, the upper layer of skin is harder than the subcutaneous tissue. When a large amount of a drug solution is injected into this upper layer of skin, aching pain is felt. Therefore, an injection amount of the drug solution into the upper layer of skin needs to be a very small amount, that is, equal to or less than 200 μL, and desirably about 100 μL.

In this regard, such an efficient syringe has been studied that such a very small amount of the drug solution can be diffused into the Langerhans cells, and the vaccine is selectively injected into the site near the epidermis in the dermic layer where many intradermal dendritic cells exist to form a bulge, where the vaccine stays for a period of time.

An example of the syringe that injects a small amount of the drug solution into the dermic layer of the upper layer of skin includes a syringe in which a tubular body that accommodates a drug solution and an injection needle assembly having an injection needle are formed independently, and the injection needle assembly is mounted to a drug solution discharging tube at a tubular end of the tubular body just before the injection.

For example, JP 2011-212185 A discloses a drug injection device including: a tubular body having a fluid chamber that accommodates a drug; a pusher section including a gasket that is mounted to a plunger and moves within the tubular body; a tubular grip section provided along an outer periphery of the tubular body; a connection section between the tubular body and an end portion of the grip section; and an injection needle assembly having a needle hub that holds an injection needle, and configured to inject, into an upper layer of skin, the drug from a needle tip slightly protruding from the needle hub. Specifically, a drug solution discharging tube at a tubular end of the tubular body is pushed and mounted into a fitting hole of the injection needle assembly.

SUMMARY

However, because the epidermic layer is thin and because of variations in the age difference, the gender difference, and the individual differences are large, a depth of an administration site near the epidermis in the dermic layer is not unambiguously defined. It is therefore difficult to uniformly determine a protruding length of the needle tip slightly protruding from the needle hub. Furthermore, when the administration is performed for a region as near the epidermis as possible in the dermic layer by means of the syringe using the tubular body that accommodates the drug solution and the injection needle assembly that injects the drug into the upper layer of skin, the possibility that the drug solution leaks from the skin is considerably high. When a needle length of the injection needle that punctures the skin is too short, the vaccine further leaks from the epidermis, and the immunity capability cannot be obtained. When the needle length is too long, the vaccine is injected into a region ranging from a site deep in the dermic layer where few intradermal dendritic cells are present to the subcutaneous tissue, and the vaccine cannot be diffused into the Langerhans cells or the intradermal dendritic cells, whereby sufficient immunity elicitation capability cannot be obtained.

As described above, even if such a syringe is used in which the needle length of the injection needle that punctures the skin is only adjusted, it is difficult to broadly inject the vaccine by a desired amount into the administration site near the epidermis in the dermic layer and form the bulge without the occurrence of the leak from the skin surface to the outside of the body, regardless of the age difference, the gender difference, and the individual differences.

Certain embodiments of the present invention have been made to solve the above-mentioned problem, and an object thereof is to provide a syringe for injecting a drug solution into an upper layer of skin that injects a drug solution such as a vaccine into an upper layer of skin, and particularly selectively into a relatively shallow site near an epidermic layer in a dermic layer to form a bulge without the occurrence of a leak from a skin surface, regardless of an age difference, a gender difference, and individual differences, whereby a sufficient drug effect, such as immunity elicitation capability, can be obtained or exhibited even by a very small amount.

A syringe for injecting a drug solution into an upper layer of skin that has been made for achieving the above-mentioned object includes: an injection needle provided with a needle hole communicating from a needle tip to a needle proximal end, the injection needle having a blade face at the needle tip; and a needle hub having a distal end portion and a proximal end portion, the needle hub holding the injection needle at the distal end portion, wherein the needle hub has a needle tip side end face, and the needle tip protrudes from the needle tip side end face, and a protruding needle length of the needle tip from the needle tip side end face is 1.15 mm±0.1 mm, and a blade face length of the blade face along an axis of the injection needle is 0.60 mm±0.15 mm.

The syringe for injecting a drug solution into an upper layer of skin may be configured such that the needle hub is provided on the same axis as the injection needle, and has an adjusting portion that causes the needle tip and the blade face to protrude and adjusts the protruding needle length, and the needle tip side end face is provided at a distal end of the adjusting portion.

The syringe for injecting a drug solution into an upper layer of skin is preferably configured such that the needle hub is provided on the same axis as the adjusting portion, and has a tubular stabilizing portion surrounding and separated from the adjusting portion.

The syringe for injecting a drug solution into an upper layer of skin is further preferably configured such that the upper layer of skin is a dermic layer of a human, and an opening of the needle hole on a side close to the needle tip is adjusted by the protruding needle length and the blade face length so as to reach a target site near epidermis in the dermic layer to be subjected to injection.

The syringe for injecting a drug solution into an upper layer of skin may include an outer cylinder inside which a drug solution is sealed and accommodated by a gasket inserted from a cylinder proximal end, the outer cylinder having a cylinder distal end provided with a drug solution discharging tube that discharges the drug solution, wherein the outer cylinder may be connected to a proximal end of the needle hub at the drug solution discharging tube.

The syringe for injecting a drug solution into an upper layer of skin preferably includes a fitting cylinder having a distal end and a proximal end, the fitting cylinder being provided with a fitting hole communicating from the distal end to the proximal end, wherein the fitting hole is preferably configured such that the proximal end portion of the needle hub is fit into the distal end and the drug solution discharging tube of the outer cylinder is fit into the proximal end.

The syringe for injecting a drug solution into an upper layer of skin may include an elastic body placed on a side close to the proximal end portion of the needle hub, and into which the injection needle is inserted.

The syringe for injecting a drug solution into an upper layer of skin is still further preferably configured such that the drug solution is a biological preparation, and the outer cylinder is a prefilled syringe.

The syringe for injecting a drug solution into an upper layer of skin may be configured such that a plunger that is pressed at 3 to 35 N to cause the drug solution to be injected into the upper layer of skin is connected to the gasket.

A syringe for injecting a drug solution into an upper layer of skin of the present invention can reliably inject a very small amount of drug solution such as a vaccine into an upper layer of skin, and particularly selectively into a relatively shallow target site near an epidermic layer in a dermic layer, regardless of an age difference, a gender difference, and an individual difference.

This syringe for injecting a drug solution into an upper layer of skin does not cause the drug solution to leak from a skin surface to the outside of the body when injecting the drug solution. Therefore, the syringe for injecting a drug solution into an upper layer of skin can reliably cause the drug solution to reach the upper layer of skin. This syringe for injecting a drug solution into an upper layer of skin causes the drug solution to reach the upper layer of skin, where a bulge is formed by the drug solution and the drug solution stays for a period of time, whereby a sufficient drug effect such as immunity elicitation capability can be obtained or exhibited even by a very small amount of the drug solution.

According to the syringe for injecting a drug solution into an upper layer of skin, therefore, even when the dose of the drug solution that is a biological preparation such as an influenza vaccine is reduced to ½ to ⅕ of that for subcutaneous administration or intramuscular administration, the immunity elicitation capability equivalent to those of these types of administration can be obtained. Consequently, immunity to a virus can be sufficiently created in the body, and the onset of an infection can be prevented. This feature also contributes to a reduction in medical expenses in medical economy.

This syringe for injecting a drug solution is configured such that, even if a drug solution discharging tube is pushed into a fitting hole with weak force at the time of the attachment of an injection needle assembly having a needle hub to an outer cylinder, because the outer cylinder and the injection needle assembly are liquid-tightly connected with pressure resistance of 3 MPa or more, the drug solution does not leak out of the syringe for injecting a drug solution.

The syringe for injecting a drug solution into an upper layer of skin can reliably cause the drug solution to reach the upper layer of skin even when the drug solution is weakly pressed by a plunger. Therefore, injection mistakes can be reduced even in a case of self-injection.

DETAILED DESCRIPTION

Hereinafter, a syringe for injecting a drug solution into an upper layer of skin according to embodiments of the present invention will be described in detail. The scope of the present invention, however, is not limited to these embodiments.

Figure 1:
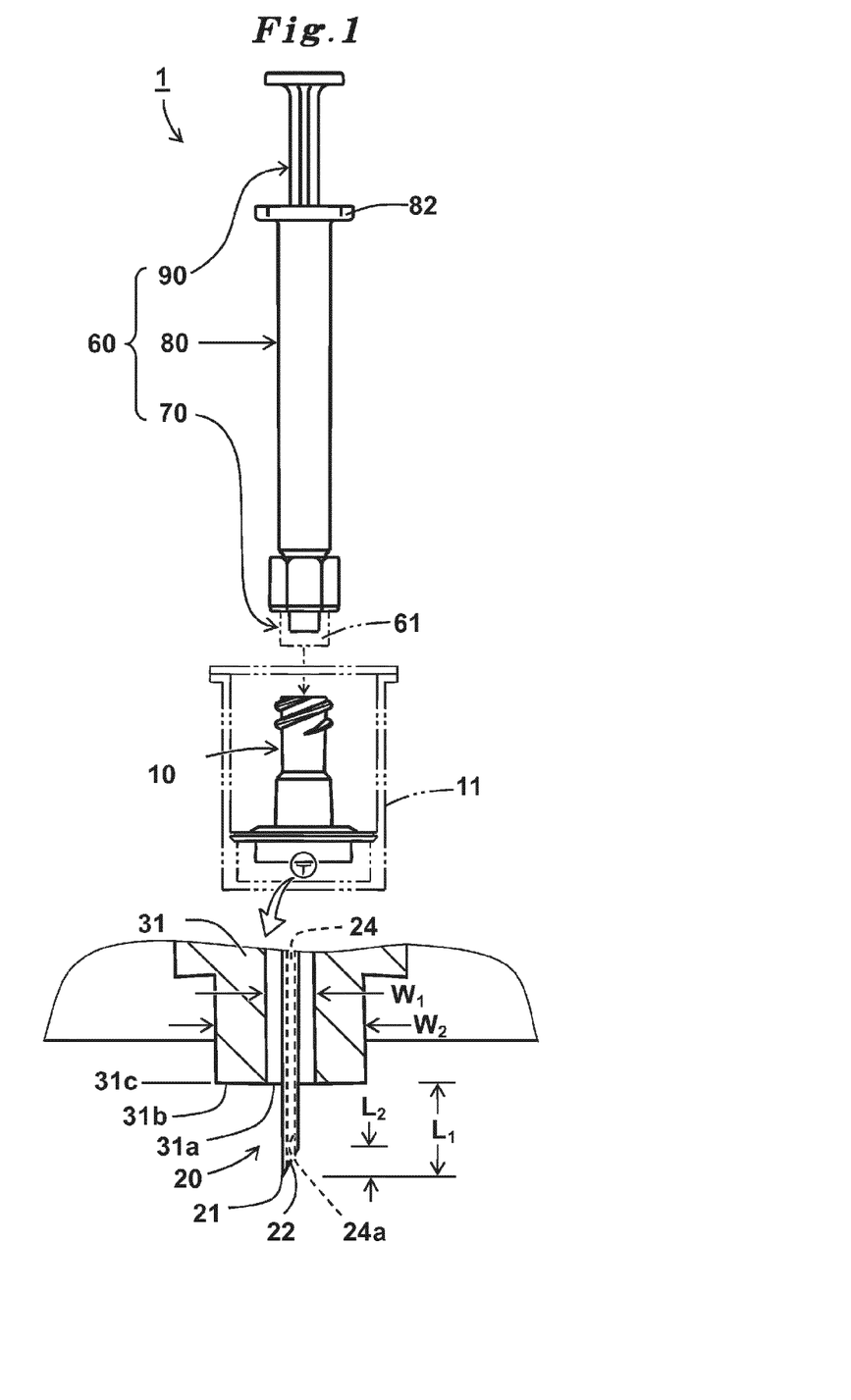
FIG. 1 is an exploded front view illustrating a syringe for injecting a drug solution into an upper layer of skin, according to an embodiment of the invention.

One embodiment of a syringe for injecting a drug solution into an upper layer of skin 1 of the present invention will be described with reference to FIG. 1. FIG. 1 is an exploded front view illustrating a state before use of the syringe for injecting a drug solution into an upper layer of skin 1. The syringe for injecting a drug solution into an upper layer of skin 1 has a syringe body 60 constituting a prefilled syringe, and an injection needle assembly 10.

This syringe for injecting a drug solution into an upper layer of skin 1 will be described in more detail with further reference to FIG. 2 which is a schematic partial cross-sectional view illustrating a state just before the syringe body 60 is mounted and connected to the injection needle assembly 10 attachably and detachably.

The syringe body 60 has a cylindrical outer cylinder 80, a drug solution discharging tube 70, a gasket 91, and a pusher 90. The drug solution discharging tube 70 is provided at a cylinder end side of the outer cylinder 80. The gasket 91 is inserted into the outer cylinder 80 from a cylinder proximal end thereof. A plunger 92 is connected to a proximal end side of the gasket 91 to form the pusher 90. A drug solution 81 is sealed between the gasket 91 and the drug solution discharging tube 70. The injection needle assembly 10 has an injection needle 20, a needle hub 30, an elastic body 40, and a fitting cylinder 50. The injection needle 20 includes a needle tube. The needle hub 30 holds the injection needle 20 with an injection needle holding portion 36. The elastic body 40 has an upper depression 46 into which the injection needle 20 is inserted. The fitting cylinder 50 accommodates the elastic body 40 and the injection needle holding portion 36 of the needle hub 30, and has a fitting hole 57 forming a female taper 54 and opening to a proximal end 58.

The syringe for injecting a drug solution into an upper layer of skin 1 is used to puncture, with a needle tip 21, an upper layer of skin of skin 100 of a person to undergo the administration to whom the drug solution 81 is to be administered, and particularly a relatively shallow target site 102a near an epidermic layer 103 in a dermic layer 102. The syringe for injecting a drug solution into an upper layer of skin 1 is then used to inject a very small amount of the drug solution 81, namely a biological preparation such as an influenza vaccine, into the upper layer of skin or the target site 102a (refer to FIG. 3), and to generate a bulge.

First, the injection needle assembly 10 will be described.

The injection needle 20 penetrates the center of the needle hub 30 to be held. The needle hub 30 has, by means of integral molding, the substantially columnar injection needle holding portion 36, an adjusting portion 31, a stabilizing portion 32, and a connection guide portion 33. The injection needle holding portion 36 holds the injection needle 20 on a side close to a needle proximal end 23 that is a needle root (upper side in FIG. 2). The adjusting portion 31 helps, at a distal end portion 31c on a side close to the needle tip 21 (lower side in FIG. 2), to inject the drug solution 81 from the injection needle 20. The stabilizing portion 32 surrounds the adjusting portion 31. The connection guide portion 33 supports the adjusting portion 31 and the stabilizing portion 32 and is linked to the injection needle holding portion 36. The injection needle 20 is configured such that the injection needle 20 coaxially penetrates the centers of the injection needle holding portion 36 and the adjusting portion 31, the needle tip 21 is exposed from the adjusting portion 31 together with a blade face 22, and, in an opposite direction, the needle proximal end 23 projects from the injection needle holding portion 36. In the middle of a body of the substantially cylindrical injection needle holding portion 36, a symmetrical adhesive filling horizontal hole 35 and a substantially cylindrical adhesive filling cavity 34 are provided. The adhesive filling horizontal hole 35 is directed to an axis and penetrates a side wall. The adhesive filling cavity 34 surrounds the injection needle 20 and is linked to the adhesive filling horizontal hole 35. The adhesive filling horizontal hole 35 and the adhesive filling cavity 34 are filled with an adhesive, and the adhesive is hardened to immovably fix the injection needle 20. The injection needle holding portion 36 is configured such that a proximal end portion 38 on a side close to the needle proximal end 23 is slightly raised around an end face and slightly widened in diameter on an outer periphery of an end portion.

The injection needle 20 includes the hollow needle tube. The injection needle 20 has the needle tip 21 and the needle proximal end 23. The needle tip 21 is exposed from the needle hub 30 of the injection needle assembly 10, and the blade face 22 forming an acute angle to an axis for puncturing the skin 100 is formed on the needle tip 21. The needle proximal end 23 is housed within the injection needle assembly 10 and formed to be substantially vertical to the axis. An opening 24a of a needle hole 24 of the needle tube opens in the blade face 22 of the injection needle 20.

Examples of the injection needle 20 include a needle tube of 26 to 33 gauges (external diameter: 0.2 to 0.45 mm), preferably 30 to 33 gauges, in size according to ISO standard for medical needle tubes (ISO9626: 1991/Amd. 1:2001(E)).

The injection needle 20 is configured such that the needle tip 21 has a protruding needle length $L_1$ of 1.15 mm±0.10 mm from the distal end portion 31c of the needle hub 30. This variation range of the protruding needle length represents a variable range of an average protruding needle length value or a range of a target protruding needle length. The variation range of the protruding needle length also sets a tolerance at the time of the manufacture of the injection needle 20 and at the time of the assembly of the injection needle assembly 10 to a maximum of 0.2 mm. The injection needle 20 is configured such that a length (blade face length) $L_2$ of the blade face 22 in an axial direction is 0.60 mm±0.15 mm. This variation range of the blade face length of the injection needle 20 represents a variable range of an average blade face length value or a target blade face length. The variation range of the blade face length also sets a tolerance at the time of the manufacture of the injection needle 20 and particularly at the time of the formation of the blade face 22 forming the acute angle to an axis of the needle tube to a maximum of 0.3 mm (refer to FIG. 1).

Figure 3:
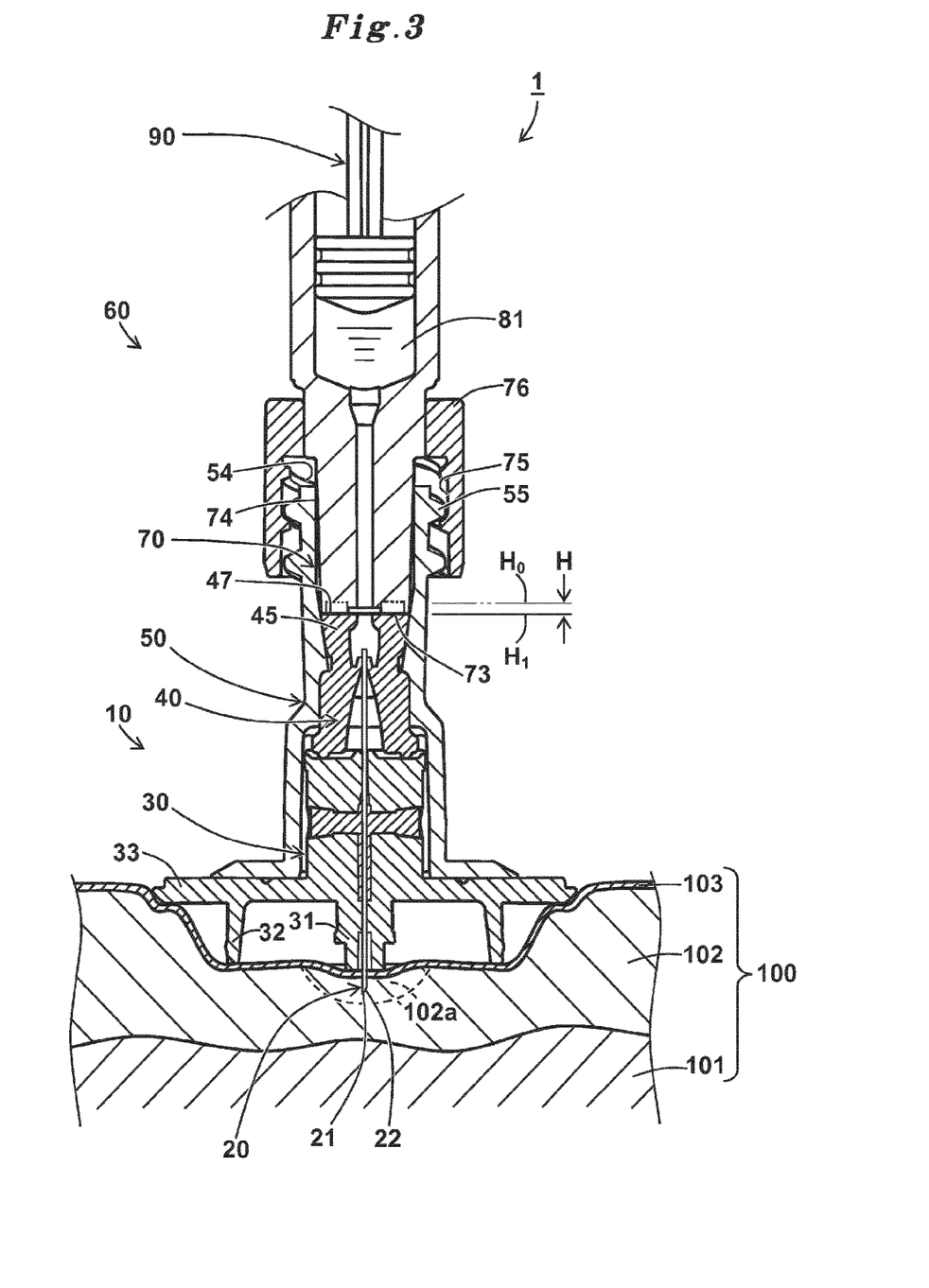
FIG. 3 is a schematic partial cross-sectional view illustrating a state in use of the syringe for injecting a drug solution into an upper layer of skin, according to an embodiment of the invention.

If the injection needle 20 is configured such that the protruding needle length $L_1$ from the needle hub 30 and the blade face length $L_2$ of the blade face 22 in the axial direction are within these ranges, a very small amount of the drug solution 81 such as a vaccine can be reliably injected into the upper layer of skin, and particularly selectively into the relatively shallow target site 102a near the epidermic layer 103 in the dermic layer 102, regardless of an age difference, a gender difference, and an individual difference (refer to FIG. 3). The protruding needle length $L_1$ from the needle hub 30 and the blade face length $L_2$ of the blade face 22 in the axial direction cooperate to cause the blade face 22 to reach the target site 102a precisely and appropriately and cause the drug solution 81 to be discharged from a needle opening of the blade face 22 to the target site 102a, whereby the bulge is formed. If any of the two is out of the range, even if the blade face reaches the skin 100, a possibility that a leak from the skin 100 occurs after the injection of the drug solution is increased, a possibility that the bulge is not formed is increased, and a possibility that the drug solution 81 including the biological preparation such as the influenza vaccine cannot be injected into the upper layer of skin, and particularly into the relatively shallow target site 102a near the epidermic layer 103 in the dermic layer 102 is increased. Because of this, a sufficient drug effect such as immunity elicitation capability can no longer be exhibited by the drug solution 81 reduced to ½ to ⅕ of that used for subcutaneous administration or intramuscular administration.

The injection needle 20 is configured such that the blade face 22 forms the acute angle of 18 to 25° to the axis of the needle tube. Owing to this acute angle, the needle tip 21 reliably punctures a skin surface to penetrate the epidermic layer 103 to reach the desired upper layer of skin, and particularly the relatively shallow target site 102a near the epidermic layer 103 in the dermic layer 102 into which the drug solution is to be injected, whereby the needle opening of the blade face 22 can be located at that site.

The syringe 1 adjusted by this injection needle 20 does not cause the drug solution 81 to leak out of the skin surface when injecting the drug solution 81 owing to the protruding needle length $L_1$ from the needle hub 30, the blade face length $L_2$ of the blade face 22 in the axial direction of the needle tube, and the blade face 22 forming the acute angle to the axis of the needle tube. Even by a very small amount of the drug solution 81, the sufficient drug effect such as the immunity elicitation capability can be obtained or exhibited because the bulge having a diameter of about a few millimeters is formed at the target site 102a by the drug solution 81, where the drug solution 81 can stay for a period of time, whereby the drug solution 81 is gradually diffused into Langerhans cells or intradermal dendritic cells, namely, immunocompetent cells. According to this syringe for injecting a drug solution into an upper layer of skin 1, even when the dose of the drug solution 81 that is the biological preparation such as the influenza vaccine is reduced to ½ to ⅕ of that for the subcutaneous administration or the intramuscular administration, a sufficient amount reaches the immunocompetent cells, and the immunity elicitation capability equivalent to that of the subcutaneous administration or the intramuscular administration can be obtained. Consequently, immunity to a virus can be sufficiently created in the body, and the onset of an infection can be prevented, regardless of the age difference such as adults, youths, infants, and babies, the gender difference, and the individual difference.

Furthermore, by using the syringe 1 adjusted to have this injection needle 20, aching pain is hardly felt when the drug solution 81 is injected into the upper layer of skin, and a dead volume caused by the drug solution 81 that has remained in the hollow of the needle tube of the injection needle 20 after the injection can be minimized.

The injection needle 20 penetrates the injection needle holding portion 36 and the adjusting portion 31, and is fixed by the adhesive in the adhesive filling horizontal hole 35 and the adhesive filling cavity 34. Before and after the injection of the drug solution 81, therefore, the injection needle 20 does not rotationally move, and the protruding needle length $L_1$ from the needle hub 30 is unchangingly maintained.

A material for the injection needle 20 is preferably, but not limited to, stainless steel, and may be aluminum, an aluminum alloy, titanium, a titanium alloy, or other metals.

The injection needle 20 is preferably configured such that puncture resistance obtained when a silicone rubber sheet of 0.5 mm is punctured at 10 mm/minute is equal to or less than 0.15 N at a maximum value of a load fluctuation curve. To an outer periphery of the injection needle 20, a lubricant such as a silicone oil may be applied. Examples of the silicone oil include a silicone oil conforming to JIS3209, and more specifically a crosslinking reaction silicone oil such as a condensed silicone oil subjected to a crosslinking reaction and an added silicone oil subjected to a crosslinking reaction. Owing to these lubricants, the injection needle 20 easily punctures the skin 100, and the aching pain of a person to undergo the administration can be reduced.

Because the injection needle 20 exists on an axis of the injection needle holding portion 36 and the adjusting portion 31, the injection needle 20 is configured to be capable of puncturing a surface of the skin 100 substantially vertically when the drug solution 81 is administered. Therefore, regardless of individual variability such as the age difference, the gender difference, and the individual difference, the injection needle 20 can certainly reach the upper layer of skin of a human, and particularly penetrate the epidermic layer 103 to reach the relatively shallow target site 102a near the epidermic layer 103 in the dermic layer 102, and only an expected amount of the drug solution 81 can be injected to reliably form the bulge (refer to FIG. 3).

The injection needle holding portion 36 of the needle hub 30 is connected to the connection guide portion 33 formed to extend in a disk shape on a side close to the needle tip 21. The connection guide portion 33 is wider in diameter than the injection needle holding portion 36. The injection needle holding portion 36 and the columnar adjusting portion 31 have the same axis, and the injection needle 20 penetrates the injection needle holding portion 36 and the columnar adjusting portion 31 to project to a needle tip side end face 31b of the adjusting portion 31. The adjusting portion 31 is depressed on a side close to the needle tip 21 in order to press and expand the epidermic layer 103 at the time of the injection of the drug solution and help to inject the drug solution 81 from the inject ion needle 20. The needle tip 21 of the injection needle 20 projects from the center of this depression 31a. The needle tip side end face 31b of the adjusting portion 31 has an area sufficiently larger than that of the bulge formed as a blister at the time of the injection of the drug solution 81 into the upper layer of skin. The adjusting portion 31 is preferably configured such that the needle tip side end face 31b has an internal diameter $W_1$ of 0.5 to 0.7 mm and an external diameter $W_2$ of 1.7 to 1.9 mm. In this range, regardless of the individual variability, only an expected amount of the drug solution 81 can be injected into the upper layer of skin of a human, and particularly into the relatively shallow target site 102a near the epidermic layer 103 in the dermic layer 102, and the leak from the skin 100 can be prevented to reliably form the bulge.

The stabilizing portion 32 is formed in a hollow cylindrical shape surrounding the adjusting portion 31, wider in diameter than the adjusting portion 31 and the injection needle holding portion 36, and thinner in diameter than the connection guide portion 33. The stabilizing portion 32 projects from the connection guide portion 33 to a side close to the needle tip 21. At the time of the injection of the drug solution, the blade face 22 of the injection needle 20 first comes into contact with the upper layer of skin, the needle tip side end face 31b of the adjusting portion 31 subsequently comes into contact with the skin surface, and the stabilizing portion 32 comes into contact with the skin surface. At this time, the adjusting portion 31 and the stabilizing portion 32 are separated so that the surface of the skin 100 is pressed and expanded and the injection needle 20 can puncture the upper layer of skin substantially vertically. The stabilizing portion 32 is preferably configured, at a distal end face thereof, such that an internal radius $W_3$ is 5.8 to 6.2 mm and an external radius $W_4$ is 6.53 to 6.57 mm. A width $L_4$ between an outer periphery of the adjusting portion 31 and an inner periphery of the stabilizing portion 32 is preferably 4.9 to 5.3 mm. The needle tip side end face 31b of the adjusting portion 31 preferably protrudes from the distal end face of the stabilizing portion 32 by a distance $L_3$ of 0.2 to 0.4 mm. In this range, the surface of the skin 100 is strained by the press on the adjusting portion 31 and the stabilizing portion 32, and regardless of the individual variability such as the age difference, the gender difference, and the individual difference, only an expected amount of the drug solution 81 is injected into the upper layer of skin of a human, and particularly into the relatively shallow target site 102a near the epidermic layer 103 in the dermic layer 102 to reliably form the bulge.

The stabilizing portion 32 preferably has a height $L_5$ of 2.9 to 3.1 mm from the distal end face of the stabilizing portion 32 to the connection guide portion 33. The connection guide portion 33 preferably has a length (width) $W_5$ of 2.9 to 3.1 mm from an outer surface of the stabilizing portion 32 to an edge of the connection guide portion 33. Owing to this feature, when the connection guide portion 33 comes into contact with the surface of the skin 100, it is indicated that the needle tip 21 of the injection needle 20 has reached the dermic layer 102.

Because the connection guide portion 33 is wider in diameter than the stabilizing portion 32, the connection guide portion 33 comes into contact with the surface of the skin 100 in a sufficient area at the time of the injection of the drug solution 81, whereby displacement of the syringe for injecting a drug solution into an upper layer of skin 1 can be prevented.

The elastic body 40 is placed on the injection needle holding portion 36 of the needle hub 30 so as to be received in an inner edge of an edge raised around an end portion of the injection needle holding portion 36 on a side close to the needle proximal end 23. The injection needle 20 is inserted into an axis of the elastic body 40 on a side close to the needle proximal end 23. The elastic body 40 has a brim 41 at an end portion thereof on a side close to the needle tip 21. The elastic body 40 has a lower depression 42 surrounding the injection needle 20 and depressed in a substantially conical shape. The elastic body 40 has an upper depression 46 surrounding the injection needle 20 and depressed in a mortar shape on a side close to the needle proximal end 23. An upper end face 47 of a protrusion 45 forming a peripheral edge surrounding the upper depression 46 is substantially flat. The upper end face 47 of the protrusion 45 has such an area as to sufficiently come into face contact with a distal end face 73 at a cylinder distal end 73a of the drug solution discharging tube 70. A diameter of an opening of the upper depression 46 of the elastic body 40 is equal to or smaller than a diameter of an opening 71 of a distal end of the drug solution discharging tube 70. The upper end face 47 of the protrusion 45 operates to come into face contact with the distal end face 73 of the drug solution discharging tube 70, and compressively deform the protrusion 45 to liquid-tightly connect the drug solution discharging tube 70 to the injection needle 20 by fitting, that is, pushing the drug solution discharging tube 70 into the fitting hole 57 of the fitting cylinder 50 (refer to FIG. 3). As a result, variations in an injection amount of a very small amount of the drug solution 81 can be reduced, and a desired bulge can be formed by an expected amount of the drug solution 81. The center of the upper depression 46 is raised around the injection needle 20 toward a side close to the needle proximal end 23, whereby a valve body 44 that uniformly presses a periphery of the injection needle 20 is formed. The injection needle 20 is sandwiched between the upper depression 46 and the lower depression 42, and supported by the elastic body 40. The needle proximal end 23 of the injection needle 20 is housed in the upper depression 46, and located slightly near a side close to the needle tip 21 rather than near the upper end face 47 of the protrusion 45. Consequently, the needle proximal end 23 of the injection needle 20 does not abut on the distal end 73 of the drug solution discharging tube 70 at the time of the injection of the drug solution. The protruding needle length $L_1$ from the needle hub 30, therefore, can be unchangingly maintained.

The fitting cylinder 50 covers the elastic body 40 and the injection needle holding portion 36 of the needle hub 30 so as to surround and accommodate the elastic body 40 and the injection needle holding portion 36 of the needle hub 30. The fitting cylinder 50 has a brim 51 at a lower end thereof, where the fitting cylinder 50 adheres or is welded to the connection guide portion 33 of the needle hub 30. Alternatively, the fitting cylinder 50 and the connection guide portion 33 are integrated in advance by means of integral molding. In the middle of the fitting cylinder 50, a diameter is smaller than that of the lower half, and a step 52 is provided. The lower half of the fitting cylinder 50 accommodates the injection needle holding portion 36 of the needle hub 30. A slightly wide diameter part 37 of the injection needle holding portion 36 of the needle hub 30 on the outer periphery of the end portion on a side close to the needle proximal end 23 abuts on an inner wall that exists in the lower half of the fitting cylinder 50, whereby backlash is prevented. The fitting cylinder 50 encompasses or presses the brim 41 of the elastic body 40 with the step 52.

The inserting cylinder 50 has the fitting hole 57. The fitting hole 57 has the female taper 54 on a needle tip side. When a taper ratio of the female taper 54 is represented in accordance with such a fraction notation that a taper ratio obtained when a diameter becomes thinner by A mm per 100 mm is represented as A/100, the female taper 54 has a taper ratio of 15/100. This is because, as described above, the syringe for injecting a drug solution is configured such that even when the drug solution discharging tube is pushed into the fitting hole with weak force of about 0.05 to 0.1 N·m at the time of the attachment of the injection needle assembly having the needle hub to the outer cylinder, because the outer cylinder and the injection needle assembly are liquid-tightly connected with pressure resistance of 3 MPa or more, a male taper 74 is fit into the female taper 54 so that at least an edge of the distal end face 73 of the male taper 74 comes into contact with the female taper 54.

The more strongly the drug solution discharging tube 70 is pushed into the fitting hole 57, the more deeply the drug solution discharging tube 70 can be fit into the fitting hole 57, with the cylinder distal end 73a of the drug solution discharging tube 70 and the female taper 54 of the fitting hole 57 made of plastic slightly deformed together.

Figure 2:
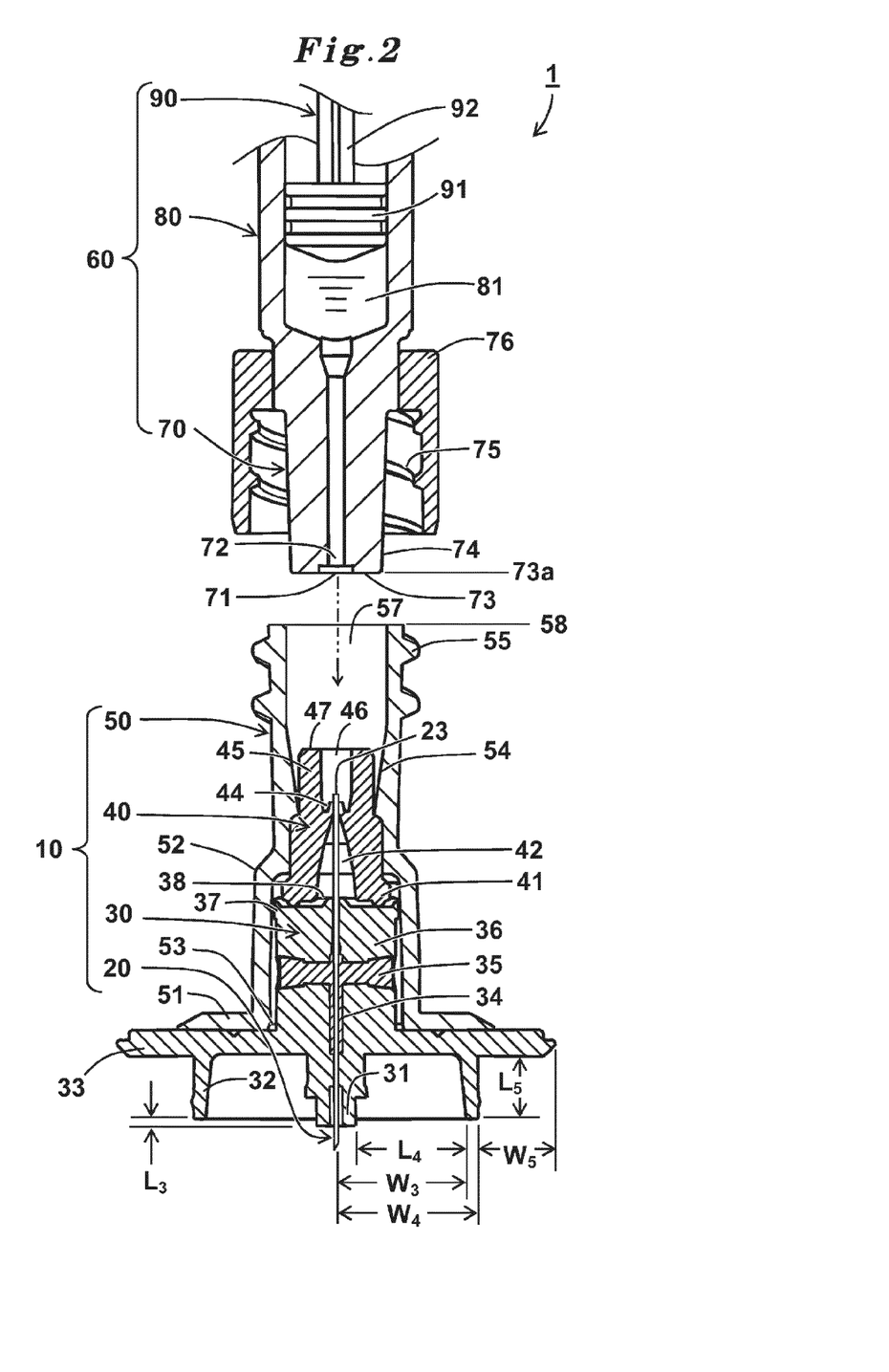
FIG. 2 is a schematic partial cross-sectional view illustrating a state before use of the syringe for injecting a drug solution into an upper layer of skin, according to an embodiment of the invention.

As illustrated in FIG. 2, in the injection needle assembly 10, the female taper 54 and the male taper 74 are adjusted so that a fitting position $H_1$ (refer to FIG. 3) of the female taper 54 of the fitting cylinder 50 and the male taper 74 of the drug solution discharging tube 70 reaches a lower side, namely, a side close to the needle tip 21, beyond the upper end face 47 of the protrusion 45 of the elastic body 40 by a height difference H (refer to FIG. 3). Before the syringe body 60 is mounted to the injection needle assembly 10, therefore, as illustrated in FIG. 2, the elastic body 40 causes the upper end face 47 of the protrusion 45 to extend in advance to an opening side of the fitting hole 57 from the fitting position $H_1$ (refer to FIG. 3) of the female taper 54 and the male taper 74 by the height difference H, and to exist at a non-fitting upper end face position $H_0$ (refer to FIG. 3). The elastic body 40 within the fitting cylinder 50 is configured such that a capacity, a height, and a shape of the protrusion 45 are appropriately adjusted so that the drug solution discharging tube 70 is fit, that is, pushed into the fitting hole 57, whereby the upper end face 47 of the protrusion 45 comes into contact with the distal end face 73 of the drug solution discharging tube 70 to be compressively deformed, and the protrusion 45 is pressed to expand to an inner wall of the fitting hole 57 and become airtight. It is more preferable that the protrusion 45 is adjusted so that, owing to the fitting, the protrusion 45 is compressively deformed and pressed to expand not only to the inner wall of the fitting hole 57 but also to the upper depression 46 and become airtight.

An outer periphery of the fitting cylinder 50 is provided with a male screw 55 that is screwed with a female screw 75 of a lock mechanism 76 formed on the syringe body 60.

An injection needle assembly cap 11 (refer to FIG. 1) that covers the needle tip 21 of the injection needle 30 together with the blade face 22 is attached to the injection needle assembly 10 until the injection needle assembly 10 is mounted to the syringe body 60 just before the injection of the drug solution 81.

Next, the syringe body 60 will be described with reference to FIG. 2. The outer cylinder 80 of the syringe body 60 has a hollow cylindrical shape to be filled with the drug solution 81. The drug solution discharging tube 70 is provided at the center on the cylinder end side of the outer cylinder 80 on the same axis. In order to push the drug solution 81 out and discharge it from the drug solution discharging tube 70, the gasket 91 is inserted into the outer cylinder 80. A space between the gasket 91 and the drug solution discharging tube 70 is filled with the drug solution 81. The drug solution 81 is liquid-tightly sealed by the gasket 91 so as not to leak. The plunger 92 is connected to the proximal end side of the gasket 91 to form the pusher 90. At a proximal end of the outer cylinder 80, a flange 82 is provided to extend in two directions from an outer periphery (refer to FIG. 1). The drug solution discharging tube 70 has a hollow hole 72, and the drug solution 81 within the outer cylinder 80 can be discharged from the hollow hole 72 to the outside of the outer cylinder 80. The male taper 74 conforming to ISO594-1 or ISO594-2 is provided at an outer periphery of the drug solution discharging tube 70. An external diameter of the male taper 74 becomes smaller toward the cylinder distal end with a taper ratio of 6/100.

At the distal end of the drug solution discharging tube 70, the flat distal end face 73 orthogonal to an axis direction is formed. In an axis part of the distal end face 73, the opening 71 of the hollow hole 72 for discharging the drug solution 81 is formed. The opening 71 is somewhat wider than a diameter of the hollow hole 72. An outer shape of the distal end face 73 of the cylinder distal end 73a of the drug solution discharging tube 70, that is, a distal end outer edge of the drug solution discharging tube 70 is formed in a circular shape. The distal end face 73 of the drug solution discharging tube 70 and a face of the male taper 74 of the drug solution discharging tube 70 are linked at the distal end outer edge of the drug solution discharging tube 70. The distal end face 73 of the drug solution discharging tube 70 has a sufficient area to come into contact with the elastic body 40 within the fitting cylinder 50 and compressively deform the elastic body 40 reliably. The distal end face 73 of the drug solution discharging tube 70 operates to come into face contact with the upper end face 47 of the protrusion 45 forming the peripheral edge of the upper depression 46 of the elastic body 40, and liquid-tightly connect the drug solution discharging tube 70 to the injection needle 20. The drug solution discharging tube 70 is closed by a drug solution discharging tube cap 61 (refer to FIG. 1) until just before the injection of the drug solution so that the drug solution 81 does not leak out and is not contaminated by external sundry bacteria.

The drug solution discharging tube 70 has, at a rear end side thereof, the tubular lock mechanism 76 surrounding the drug solution discharging tube 70 on the same axis. A cross-section of the tube of the lock mechanism 76 has a circular inner periphery, and an outer periphery is formed in a hexagonal shape so as to be, for example, easily pinched and rotated. The lock mechanism 76 is formed of a member different from those of the outer cylinder 80 and the drug solution discharging tube 70, and attached to a proximal end side of the drug solution discharging tube 70 by means of adhesion, fitting, and screwing or the like. Alternatively, the lock mechanism 76 is formed together with the outer cylinder 80 and the drug solution discharging tube 70 by means of integral molding. When the drug solution discharging tube 70 is fit into the fitting hole 57 of the fitting cylinder 50, the more deeply the lock mechanism 76 is screwed, the more strongly the drug solution discharging tube 70 can be fit into the fitting hole 57 of the fitting cylinder 50. Therefore, the more deeply the lock mechanism 76 is screwed, the more strongly the distal end face 73 of the drug solution discharging tube 70 pushes the protrusion 45 of the elastic body 40. However, even if the drug solution discharging tube 70 is strongly fit into the fitting hole 57 of the fitting cylinder 50, the extent of deformation of the male taper 74 and the female taper 54 is limited. The fitting position $H_1$ (refer to FIG. 3), therefore, is determined in accordance with the taper ratio, dimensional tolerance, materials for the drug solution discharging tube 70 and the fitting cylinder 50, and the degree of tightness of the lock mechanism 76.

The syringe body 60, the lock mechanism 76 thereof, the fitting cylinder 50 and the needle hub 30 of the injection needle assembly 10, and the plunger 92 of the pusher 90 are formed of plastic such as a thermoplastic resin and a thermosetting resin and/or metal. Examples of the plastic include polypropylene, polycarbonate, polyethylene, and a cycloolefin polymer. Examples of the metal include stainless steel and aluminum. The elastic body 40 and the gasket 91 are formed of: various types of rubber such as natural rubber and silicone rubber; various types of thermoplastic elastomers such as a polyurethane-based elastomer and a styrene-based elastomer; or an elastic material including a mixture of these various types of rubber and various types of thermoplastic elastomers.

The syringe for injecting a drug solution into an upper layer of skin 1 is manufactured as follows. First, the injection needle assembly 10 is manufactured in the following way. The needle hub 30 and the fitting cylinder 50 are each molded from a plastic material, and the elastic body 40 is molded from a rubber material. The injection needle 20 is put into the injection needle holding portion 36 of the needle hub 30 and a through hole of the adjusting portion 31 on the same axis. While the needle tip 21 of the injection needle 20 protrudes from the distal end portion 31c of the adjusting portion 31 by a desired length for puncturing the skin 100, the adhesive is poured from the adhesive filling horizontal hole 35 formed in the injection needle holding portion 36 to adhesively fix the injection agent holding portion 36 and the injection needle 20. The elastic body 40 is inserted into the fitting cylinder 50, and the brim 41 of the elastic body 40 is locked in the step 52 of the fitting cylinder 50. The adhesive is applied to a contact part of the brim 51 of the fitting cylinder 50 and the connection guide portion 33 of the needle hub 30. Next, the needle hub 30 is inserted into the fitting cylinder 50 together with the injection needle 20, and the elastic body 40 is penetrated from a side close to the needle proximal end 23 of the injection needle 20. After that, the brim 51 of the fitting cylinder 50 and the connection guide portion 33 of the needle hub 30 are adhesively fixed to form the injection needle assembly 10. The injection needle assembly 10 is housed in the injection needle assembly cap 11. The injection needle assembly cap 11 is sealed and tightly closed with a lid by heat welding, and sterilized as necessary.

Meanwhile, the syringe body 60 is manufactured in the following way. The outer cylinder 80, the drug solution discharging tube 70, and the lock mechanism 76 are each molded from a plastic material integrally. The gasket 91 is molded from a rubber material, and the plunger 92 is molded from a plastic material. After that, the gasket 91 is connected to the plunger 92 to produce the pusher 90. The syringe body 60 is closed by the drug solution discharging tube cap 61, and the outer cylinder of the syringe body 60 is filled with the drug solution 81. A filling amount of the drug solution 81 is, for example, such a dose of the drug solution 81 as to be increased from a desired injection amount for the upper layer of skin (for example, 100 to 200 µL) by a dead volume capacity that only slightly occurs. The outer cylinder is filled with this dose of the drug solution 81. The gasket 91 of the pusher 90 is then inserted together with the plunger 92 to form the syringe body 60 that is a prefilled syringe. The syringe body 60 is housed in a sterilization bag. The sterilization bag is tightly closed, and sterilized as necessary.

Next, a usage will be described with reference to FIG. 3 for connecting the syringe body 60 to the injection needle assembly 10 by fitting, that is, pushing the drug solution discharging tube 70 into the fitting hole 57 of the fitting cylinder 50, and for injecting the drug solution 81 into the upper layer of skin.

The syringe body 60 and the injection needle assembly 10 are opened (refer to FIG. 1). The drug solution discharging tube 70 of the syringe body 60 is lightly pushed into the fitting cylinder 50 of the injection needle assembly 10. After that, the female screw 75 of the tubular lock mechanism 76 surrounding the drug solution discharging tube 70 is screwed with the male screw 55 of the fitting cylinder 50 of the injection needle assembly 10, and tightening is started with a torque of about 0.05 to 0.4 N·m. Then, the drug solution discharging tube 70 is inserted into the fitting cylinder 50 further deeply.

When the lock mechanism 76 is tightened, the distal end face 73 of the drug solution discharging tube 70 first abuts on the upper end face 47 of the protrusion 45 of the elastic body 40 precisely at the non-fitting upper end face position $H_0$. When the lock mechanism 76 is further tightened, the female screw 75 and the male screw 55 are screwed with each other further deeply, and the distal end face 73 of the drug solution discharging tube 70 starts to compressively deform the protrusion 45 of the elastic body 40 while strongly in contact with the protrusion 45. When the lock mechanism 76 is still further tightened, the protrusion 45 is pushed further strongly at the upper end face 47, the male taper 74 of the drug solution discharging tube 70 is precisely fit into the female taper 54 of the fitting hole 57 of the fitting cylinder 50, and the tightening cannot be performed any more. Then, the protrusion 45 of the elastic body 40 is compressively deformed to reach the fitting position $H_1$ of the male taper 74 and the female taper 54.

After that, the injection needle assembly cap 11 is removed. A side of the injection needle assembly 10 close to the needle tip 21 is directed to the skin 100. The syringe for injecting a drug solution into an upper layer of skin 1 is pressed so that the injection needle 20 is vertical to the skin 100. The needle tip 21 punctures the skin 100, and the stabilizing portion 32 is simultaneously placed firmly on the epidermic layer 103 of the skin 100. The adjusting portion 31 comes into contact with the epidermic layer 103 of the skin 100, and the stabilizing portion 32 and the adjusting portion 31 strain a surface of the epidermic layer 103. The connection guide portion 33 comes into contact with the skin 100 and becomes stable so that the syringe for injecting a drug solution 1 is not stirred. The injection needle 20 penetrates the epidermic layer 103 by means of the acute-angled blade face 22 of the needle tip 21. The needle opening of the blade face 22 precisely reaches the relatively shallow target site 102a near the epidermic layer 103 in the dermic layer 102 of the upper layer of skin to be subjected to the injection. The needle opening of the blade face 22, however, does not reach subcutaneous tissue 101. The pusher 90 is then completely pushed to inject the drug solution 81. At this time, because the elastic body 40 has already been sufficiently compressively deformed, the elastic body 40 is not compressively deformed any more by the pressure applied to the drug solution 81 by the pusher 90. The drug solution 81 remains at the target site 102a to be subjected to the injection, and does not leak to the epidermic layer 103. After that, the injection needle 20 is pulled out, and the syringe for injecting a drug solution into an upper layer of skin 1 is separated from the skin 100. Then, the bulge is formed by the drug solution 81 that remains at the target site 102a to be subjected to the injection. The bulge is like a red macule of a few millimeters and slightly swells toward the outside. The syringe for injecting a drug solution into an upper layer of skin 1 is closed by the injection needle assembly cap 11 (refer to FIG. 1) again, and discarded as medical waste.

EXAMPLES

A syringe for injecting a drug solution into an upper layer of skin according to an embodiment of the invention and a syringe for injecting a drug solution in which the present invention is not applied were produced experimentally, and the injection of a drug solution into an upper layer of skin was tested. These examples are described below.

Examples and Comparative Examples

The syringe for injecting a drug solution into an upper layer of skin of the present invention illustrated in FIGS. 1 to 3 was produced experimentally. Its injection needle has the protruding needle length $L_1$ from the needle hub and the blade face length $L_2$ of the blade face in the axial direction represented in Table 1. The injection needle has 33 gauges and is configured such that puncture resistance obtained when a silicone rubber sheet of 0.5 mm is punctured at 10 mm/minute is equal to or less than 0.15 N at a maximum value of a load fluctuation curve. Saline was used as the drug solution.

The distance $L_3$ by which the needle tip side end face 31b of the adjusting portion 31 protrudes from the distal end face of the stabilizing portion 32 is 0.3 mm. The width $L_4$ between the outer periphery of the adjusting portion 31 and the inner periphery of the stabilizing portion 32 is 5.1 mm. The height $L_5$ from the distal end face of the stabilizing portion 32 to the connection guide portion 33 is 3.0 mm. The stabilizing portion 32 has, at the distal end face thereof, the internal radius $W_3$ of 6.0 mm. The external radius $W_4$ of the stabilizing portion 32 is 6.55 mm. The length (width) $W_5$ from the outer surface of the stabilizing portion 32 to the edge of the connection guide portion 33 is 3.0 mm.

longitudinal length/2×lateral length/2]. Furthermore, regarding the administration to the relatively shallow target site near the epidermic layer in the dermic layer of the adult, it was also examined whether the administration succeeded without the leak, the administration was performed but the leak occurred, or the administration was performed for a site deeper than the target site. The results are summed up and shown in Table 1. Pressing force of the syringe for injecting a drug solution was 3 to 35 N for all the examples.

TABLE 1

| | INJECTION NEEDLE OF SYRINGE FOR INJECTING DRUG SOLUTION | | RESULT AFTER INJECTION OF DRUG SOLUTION USING SYRINGE FOR INJECTING DRUG SOLUTION | | | |
| --- | --- | --- | --- | --- | --- | --- |
| | PROTRUDING NEEDLE LENGTH $L_1$ [UPPER LINE IS AVERAGE (mm)] [LOWER LINE IS VARIATION (mm)] | BLADE FACE LENGTH $L_2$ OF BLADE FACE [UPPER LINE IS AVERAGE (mm)] [LOWER LINE IS VARIATION (mm)] | RATIO OF LEAK FROM SKIN [THE NUMBER OF LEAK CASES/ THE NUMBER OF TESTS] | AVERAGE BULGE AREA (mm$^2$) | t-TEST FOR BULGE AREA RELATIVE TO EXAMPLE 1 (NUMBER IN PARENTHESES IS P VALUE) | STATE OF ADMINISTRATION TO TARGET SITE |
| EXAMPLE 1 | 1.15 (1.12-1.18) | 0.75 (0.73-0.77) | 0/32 (0%) | 56 | — | SUCCEED |
| EXAMPLE 2 | 1.15 (1.12-1.18) | 0.45 (0.43-0.47) | 0/32 (0%) | 53 | NOT SIGNIFICANTLY DIFFERENT (0.97) | SUCCEED |
| COMPARATIVE EXAMPLE 1 | 1.00 (0.97-1.03) | 0.45 (0.43-0.47) | 1/46 (2%) | 52 | NOT SIGNIFICANTLY DIFFERENT (0.95) | LEAK |
| COMPARATIVE EXAMPLE 2 | 1.00 (0.97-1.03) | 0.75 (0.73-0.77) | 5/50 (10%) | 54 | NOT SIGNIFICANTLY DIFFERENT (0.97) | LEAK |
| COMPARATIVE EXAMPLE 3 | 1.30 (1.27-1.33) | 0.45 (0.43-0.47) | 0/51 (0%) | 40 | SIGNIFICANTLY DIFFERENT (<0.01) | DEEP |
| COMPARATIVE EXAMPLE 4 | 1.30 (1.27-1.33) | 0.75 (0.73-0.77) | 0/51 (0%) | 43 | SIGNIFICANTLY DIFFERENT (<0.01) | DEEP |

Into each of 80 adult men and women volunteers, 100 μL of the drug solution was injected using the syringe for injecting a drug solution into an upper layer of skin. A procedure for this is as follows. A site in a shoulder of an upper arm to be subjected to the administration was disinfected with ethanol for disinfection, and skin around the site was strained. After the syringe body was fit with the injection needle assembly, the injection needle assembly cap was removed, and the syringe for injecting a drug solution was held so that the pusher was enabled to be pushed by a thumb. The syringe for injecting a drug solution was vertically pressed against the skin until the connection guide portion came into contact with the skin in such a manner that the site to be subjected to the administration was tapped with the needle hub of the syringe for injecting a drug solution. The needle tip then punctured the skin, and the pusher was pushed by the thumb to slowly inject the drug solution into the upper layer of skin. The pusher was completely pushed and held for about two seconds. After that, the syringe for injecting a drug solution was separated from the skin so that the injection needle was pulled out. The presence or absence of the leak of the drug solution from the skin surface was visually checked, and the presence or absence of the formation of the bulge was visually checked. When the bulge was formed, lengths in longitudinal and lateral directions of the bulge were measured using a vernier scale, and a bulge area was calculated in accordance with [circular constant×

In Example 1 and Example 2, although the areas of the bulges were equivalent to those of Comparative Example 1 and Comparative Example 2, leaks from the skin did not occur. In other words, the administration was able to be performed for a region near the epidermis in the dermic layer of the upper layer of skin.

On the other hand, in Comparative Example 1 and Comparative Example 2, although the areas of the bulges were equivalent to those of Example 1 and Example 2, leaks from the skin were observed in 2 to 10%. In other words, when the administration is performed for a region near the epidermis in the dermic layer of the upper layer of skin, the administration might not be sufficiently performed for the dermic layer.

Although the leaks from the skin were not observed in Comparative Example 3 and Comparative Example 4, the areas of the bulges were smaller than those of Example 1, Example 2, Comparative Example 1, and Comparative Example 2. In other words, it was found that the administration was performed for a part deep in the dermic layer.

To sum up, Example 1 and Example 2 were found to each have the most suitable needle protruding length $L_1$ and blade face length $L_2$ for the success of the administration to the shallow target site near the epidermic layer in the dermic layer without the occurrence of the leak from the skin.

According to the syringe for injecting a drug solution into an upper layer of skin of the present invention, the leak from the skin is not observed after the injection of the drug solution, the administration can be reliably performed for the upper layer of skin, and particularly for the relatively shallow target site near the epidermic layer in the dermic layer, and a very small amount of the drug solution such as the vaccine can be reliably injected into the upper layer of skin, and particularly selectively into the relatively shallow target site near the epidermic layer in the dermic layer, regardless of the individual variability such as the age difference, the gender difference, and the individual difference of the adults.

INDUSTRIAL APPLICABILITY

A syringe for injecting a drug solution into an upper layer of skin of the present invention is used to inject a small amount of drug solution into an upper layer of skin of a patient.

REFERENCE SIGNS LIST 1 syringe for injecting drug solution into upper layer of skin
10 injection needle assembly
11 injection needle assembly cap
20 injection needle
21 needle tip
22 blade face
23 needle proximal end
24 needle hole
24a opening of needle hole
30 needle hub
31 adjusting portion
31a depression
31b needle tip side end face
31c distal end portion
32 stabilizing portion
33 connection guide portion
34 adhesive filling cavity
35 adhesive filling horizontal hole
36 injection needle holding portion
37 wide diameter part
38 proximal end portion
40 elastic body
41 brim
42 lower depression
44 valve body
45 protrusion
46 upper depression
47 upper end face
50 fitting cylinder
51 brim
52 step
54 female taper
55 male screw
57 fitting hole
58 proximal end
60 syringe body
61 drug solution discharging tube cap
70 drug solution discharging tube
71 opening
72 hollow hole
73 distal end face
73a cylinder distal end
74 male taper
75 female screw
76 lock mechanism
80 outer cylinder
81 drug solution
82 flange
90 pusher
91 gasket
92 plunger
100 skin
101 subcutaneous tissue
102 dermic layer
102a target site
103 epidermic layer
H height difference
$H_0$ non-fitting upper end face position
$H_1$ fitting position
$L_1$ protruding needle length from needle hub
$L_2$ blade face length in axial direction
$L_3$ distance between end face of adjusting portion and end face of stabilizing portion
$L_4$ width between outer periphery of adjusting portion and inner periphery of stabilizing portion
$L_5$ height from distal end face of stabilizing portion to connection guide portion
$W_1$ internal diameter of end face of adjusting portion
$W_2$ external diameter of end face of adjusting portion
$W_3$ internal radius of end face of stabilizing portion
$W_4$ external radius of end face of stabilizing portion
$W_5$ length from outer surface of stabilizing portion to edge of connection guide portion

What is claimed is:

1. A syringe for injecting a drug solution into a dermic layer of a human, comprising:
    an injection needle having a needle hole communicating from a needle tip to a needle proximal end, the injection needle having a blade face at the needle tip; and
    a needle hub having a distal end portion and a proximal end portion, the needle hub holding the injection needle at the distal end portion,
    wherein the needle hub has a needle tip side end face, and the needle tip protrudes from the needle tip side end face,
    wherein a protruding needle length of the needle tip from the needle tip side end face is 1.15 mm±0.1 mm, and a blade face length of the blade face along an axis of the injection needle is 0.60 mm±0.15 mm, and
    wherein a location of an opening of the needle hole on a side close to the needle tip, based on the protruding needle length and the blade face length, is such that a target site near an epidermis in the dermic layer can be subjected to injection.

2. The syringe according to claim 1, wherein
    the needle hub is located on the same axis as the injection needle, and includes an adjusting portion from which the needle tip protrudes, wherein the protruding needle length is a length from which the needle tip protrudes from the adjusting portion, and
    the needle tip side end face is provided at a distal end of the adjusting portion.

3. The syringe according to claim 2, wherein the needle hub is located on the same axis as the adjusting portion, and has a tubular stabilizing portion surrounding and separated from the adjusting portion.

4. The syringe according to claim 1, further comprising:
    an outer cylinder inside which a drug solution is disposed and sealed by a gasket, the outer cylinder having a cylinder distal end that includes a drug solution discharging tube configured to discharge the drug solution, wherein the outer cylinder is connected to the proximal end portion of the needle hub at the drug solution discharging tube.

5. The syringe according to claim 4, further comprising:
a fitting cylinder having a distal end and a proximal end, the fitting cylinder including a fitting hole communicating from the distal end to the proximal end,
wherein the proximal end portion of the needle hub is fit into fitting hole at the distal end of the fitting cylinder and the drug solution discharging tube of the outer cylinder is fit into the fitting hole at the proximal end of the fitting cylinder.

6. The syringe according to claim 4, wherein:
the drug solution is a biological preparation, and
the outer cylinder is a prefilled syringe.

7. The syringe according to claim 4, wherein:
a plunger is connected to the gasket, and
the plunger is configured such that a pressing force of 3 to 35 N causes the drug solution to be injected into the dermic layer.

8. The syringe according to claim 1, further comprising an elastic body located on a side close to the proximal end portion of the needle hub, the elastic body supporting the injection needle.

* * * * *